United States Patent
Kleiner

(10) Patent No.: US 6,878,843 B2
(45) Date of Patent: Apr. 12, 2005

(54) METHOD FOR PREPARING HYDROXYPHENYL CARBOXYLIC ACID ESTERS

(75) Inventor: Christoph Kleiner, Gipf-Oberfrick (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 10/311,724

(22) PCT Filed: Jun. 14, 2001

(86) PCT No.: PCT/CH01/00370

§ 371 (c)(1),
(2), (4) Date: May 6, 2003

(87) PCT Pub. No.: WO01/98249

PCT Pub. Date: Dec. 27, 2001

(65) Prior Publication Data

US 2003/0166962 A1 Sep. 4, 2003

(30) Foreign Application Priority Data

Jun. 23, 2000 (CH) .............................................. 1251/00
Feb. 22, 2001 (CH) .............................................. 0312/01

(51) Int. Cl.$^7$ ............................................. C07C 69/76
(52) U.S. Cl. .............................. 560/75; 560/76; 560/67
(58) Field of Search ............................. 560/75, 76, 67; 546/226

(56) References Cited

U.S. PATENT DOCUMENTS

| | | | | |
|---|---|---|---|---|
| 3,644,482 A | * | 2/1972 | Dexter et al. .................. | 560/75 |
| 4,536,593 A | * | 8/1985 | Orban et al. .................. | 560/75 |
| 4,594,444 A | | 6/1986 | Orban ........................ | 560/67 |
| 4,716,244 A | | 12/1987 | Orban ........................ | 560/75 |
| 5,206,414 A | * | 4/1993 | Evans et al. .................. | 560/75 |
| 5,481,023 A | | 1/1996 | Kleiner et al. ................ | 560/75 |
| 5,563,291 A | | 10/1996 | Kleiner | |
| 5,892,097 A | * | 4/1999 | Ross et al. ................... | 560/75 |
| 6,248,899 B1 | | 6/2001 | Pugin et al. | |
| 2002/0022731 A1 | | 2/2002 | Pugin et al. ............. | 548/262.4 |

FOREIGN PATENT DOCUMENTS

| | | | |
|---|---|---|---|
| EP | 0469331 | | 2/1992 |
| EP | 0608089 | * | 7/1994 |
| GB | 1081789 | | 8/1967 |
| GB | 1103145 | | 2/1968 |

\* cited by examiner

*Primary Examiner*—Rita Desai
*Assistant Examiner*—Hector M. Reyes
(74) *Attorney, Agent, or Firm*—Tyler A. Stevenson

(57) ABSTRACT

A process for the preparation of a compound of formula (I)

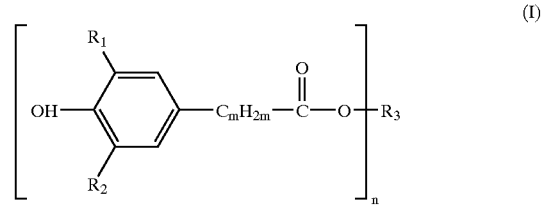

wherein $R_1$ and $R_2$ are each independently of the other $C_1$–$C_8$alkyl, cyclopentyl or cyclohexyl,
m is 1, 2 or 3, preferably 2,
n is an integer from 1 to 30, and
$R_3$ is an n-valent radical from linear or branched $C_4$–$C_{30}$alkyl, which is optionally interrupted by one or more oxygen atoms, or (when n=1–12) an n-valent radical from $C_5$–$C_{12}$cycloalkyl, or a radical $R_4$—[$NR_5$—$C_mH_{2m}$—]$_p$,
$R_4$ is hydrogen, an n-valent radical from linear or branched $C_4$–$C_{30}$alkyl, which is optionally interrupted by one or more —$NR_5$— groups, or (when n=1–12) an n-valent radical from $C_5$–$C_{12}$cycloalkyl,
$R_5$ radicals, each independently of any other(s), are hydrogen or methyl or —$C_mH_{2m}$—, preferably hydrogen, and
p corresponds to the number of —[$NR_5$—$C_mH_{2m}$—] groups that gives n —$C_mH_{2m}$— radicals per molecule,
by reaction of a compound of formula (II)

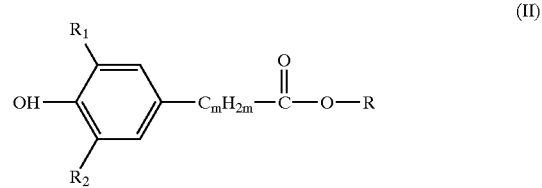

wherein R is $C_1$–$C_3$alkyl,
with a compound of formula (III)

$$R_3(OH)_n \qquad (III)$$

wherein $R_3$ and n have the definitions given, wherein the reaction takes place at a practically neutral acid value (pH) and in the presence of at least one alkali metal salt of an organic carboxylic acid, which salt is dissolved or suspended in the reaction mixture, or in the presence of a mixture of such alkali metal salts, (i) that alkali metal salt being formed from an alkali metal cation and an anion of an organic carboxylic acid and (ii) the organic carboxylic acid being at least partially volatile under the reaction conditions applied. Preferred alkali metal salts are alkali metal formate and alkali metal acetate.

20 Claims, No Drawings

METHOD FOR PREPARING HYDROXYPHENYL CARBOXYLIC ACID ESTERS

The invention relates to a process for the preparation of hydroxyphenylcarboxylic acid esters using selected catalysts. The invention relates also to novel hydroxyphenylcarboxylic acid esters that can be prepared according to the process of the invention.

Hydroxyphenylcarboxylic acid esters, especially those of the general formula (I), are used especially as antioxidants. A large number of compounds of formula (I) is known. They can be prepared, for example, by transesterification with suitable catalysts. Such transesterification procedures are described, for example, in U.S. Pat. Nos. 4,716,244; 5,481,023; 5,563,291.

Some compounds of formula (I) are important commercial products. For example they protect organic materials, such as plastics and lubricants, against thermal, oxidative and/or actinic degradation. There continues to be a need for such novel compounds for use as antioxidants and for improved processes for their preparation.

It has now been found that, in the transesterification process known per se, selected carboxylic acid salts of alkali metals, for example lithium acetate, sodium acetate or potassium acetate, can surprisingly be used as catalysts in a practically neutral medium and without solvents, the products obtained being in the form of colourless melts that can be used directly and without further purification procedures. It is also surprising that neutralisation of the catalyst is not necessary and back-esterification reactions do not occur, even when the fully reacted cooled reaction mass comes into contact with alcohols. It is remarkable that, under the conditions specified, especially neutral pH and without the use of solvents, the said catalysts catalyse transesterifications in which n may be 1, 2, 3, 4 or higher.

The present invention is defined in the claims. The present invention relates especially to a process for the preparation of compounds of formula (I)

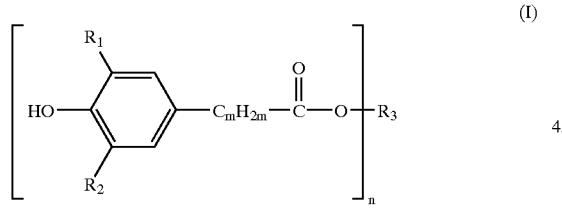

wherein
$R_1$ and $R_2$ are each independently of the other $C_1$–$C_8$alkyl, cyclopentyl or cyclohexyl,
m is 1, 2 or 3, preferably 2,
n is an integer from 1 to 30, preferably an integer from 1 to 10, especially 1, 2, 3, 4, 5 or 6, and preferably 1, 2, 3 or 4,
$R_3$ is an n-valent radical from linear or branched $C_4$–$C_{30}$alkyl, which is optionally interrupted by one or more oxygen atoms, or (when n=1–12) an n-valent radical from $C_5$–$C_{12}$cycloalkyl, or is a radical $R_4$—[$NR_5$—($C_mH_{2m}$)—]$_p$,
$R_4$ is hydrogen, an n-valent radical from linear or branched $C_4$–$C_{30}$alkyl, which is optionally interrupted by one or more —$NR_5$— groups, or (when n=1–12) an n-valent radical from $C_5$–$C_{12}$cycloalkyl,
$R_5$ radicals, each independently of any other(s), are hydrogen or methyl or —($C_mH_{2m}$)—, preferably hydrogen, and p corresponds to the number of —[$NR_5$—($C_mH_{2m}$)—] groups that gives n—($C_mH_{2m}$)— radicals per molecule,
by, reaction of a compound of formula (II)

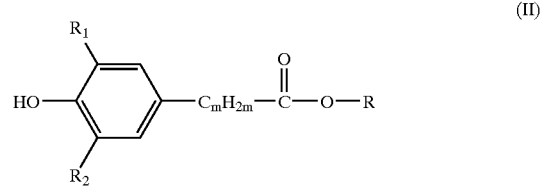

wherein R is $C_1$–$C_3$alkyl,
with a compound of formula (III)

$$R_3(OH)_n \quad (III)$$

wherein $R_3$ and n are as defined above,
wherein the reaction takes place at a practically neutral acid value (pH) and in the presence of at least one alkali metal salt of an organic carboxylic acid, which salt is dissolved or suspended in the reaction mixture, or in the presence of a mixture of such alkali metal salts, (i) that alkali metal salt being formed from an alkali metal cation and an anion of an organic carboxylic acid and (ii) the organic carboxylic acid being at least partially volatile under the reaction conditions applied.

The reaction conditions applied in the reaction are preferably temperatures in the range from 50° C. to 250° C., especially from 80° C. to 220° C., more especially from 140° C. to 220° C., and pressures in the range from 0.1 mbar to 1 atm (normal pressure), preferably from 0.1 mbar to 100 mbar, especially from 0.1 mbar to 50 mbar and more especially from 0.1 mbar to 20 mbar. The salt-forming carboxylic acids preferably have a boiling point that lies within the mentioned temperature and pressure ranges.

As salt-forming cations of alkali metals there come into consideration especially lithium, sodium and potassium cations. Sodium, potassium and/or lithium cations and hence sodium, potassium and/or lithium salts of organic carboxylic acids are preferred.

Examples of carboxylic acids that in their acid form are at least partially volatile under the reaction conditions applied include aliphatic, saturated or unsaturated carboxylic acids having preferably from 2 to 10 carbon atoms, especially from 2 to 6 carbon atoms, for example formic acid, acetic acid, propionic acid, n-butyric acid, isobutyric acid, n-valeric acid, trimethylacetic acid, caproic acid, n-heptanoic acid or pelargonic acid. Further examples include malonic acid, maleic acid, fumaric acid and also malonic acid monomethyl ester. Halogenated acids are also suitable, for example fluoroacetic acid, chloroacetic acid, bromoacetic acid, difluoroacetic acid, dichloroacetic acid, trifluoroacetic acid, trichloroacetic acid, α-chloropropionic acid or β-chloropropionic acid. Preference is given to sodium acetate, potassium acetate, lithium acetate, sodium formate, potassium formate and lithium formate or a mixture of such compounds.

The catalyst is preferably added in amounts of from 0.05 to 5 mol %, based on the molar amount of the compound of formula (I) to be reacted.

$R_1$ is preferably $C_1$–$C_8$alkyl, that alkyl radical being linear or branched. $R_1$ is preferably an alkyl radical having from 1 to 4 carbon atoms, especially methyl, ethyl, propyl or butyl. $R_1$ is preferably a branched radical, especially methyl or tert-butyl.

$R_2$ is preferably $C_1$–$C_8$alkyl, that alkyl radical being linear or branched. $R_2$ is preferably an alkyl radical having from 1 to 4 carbon atoms, especially methyl, ethyl, propyl or butyl. $R_2$ is preferably a branched radical, especially methyl or tert-butyl, preferably tert-butyl.

Compounds of formula (I) may contain phenyl radicals differently substituted by $R_1$ and $R_2$ in the same molecule, and $R_1$ and $R_2$ on the same phenyl radical may be identical or different. Accordingly, for example, $R_1$ and $R_2$ may both be methyl or tert-butyl, or $R_1$ may be methyl and $R_2$ tert-butyl.

$R_3$ as an n-valent alkyl radical having from 4 to 30 carbon atoms that is optionally interrupted by oxygen may be linear or branched or may be in the form of a mixture. Such mixtures may consist of compounds in which $R_3$ is a mixture of predominantly linear or branched alkyl radicals, for example having 14, 16, 18 and 20 carbon atoms, it also being possible for some of those alkyl radicals to be branched.

When $R_3$ is a radical $R_4$—[$NR_5$—($C_mH_{2m}$)—]$_p$, that radical is preferably $R_4$—[NH—($C_mH_{2m}$)—]$_p$ or $R_4$—[N($C_mH_{2m}$)$_2$—]$_p$, and especially $R_4$[NH—($C_mH_{2m}$)—]$_p$. $R_4$ therein is preferably an alkyl radical having from 4 to 30 carbon atoms that is optionally interrupted by —$NR_5$—, preferably by —NH—, and may be linear or branched, for example having 14, 16, 18 and 20 carbon atoms. $R_4$ can also be derived (when n=2) from alkylenediamine, such as ethylenediamine or propylenediamine, or from a polyalkylenediamine, preferably a dialkylenediamine, such as diethylenediamine or dipropylenediamine.

When n=1, $R_3$ is preferably a monovalent radical, preferably n-butyl, isobutyl, tert-butyl, pentyl, isopentyl, hexyl, heptyl, octyl, 2-ethylhexyl, nonyl, decyl, undecyl, dodecyl, tridecyl, tetradecyl, pentadecyl, hexadecyl, heptadecyl, octadecyl, eicosyl and the corresponding homologous radicals having carbon atoms increasing to 30 carbon atoms or a mixture of such $C_4$–$C_{30}$ radicals. When n=1, $R_3$ is preferably also a monovalent radical such as cycloalkyl having from 5 to 12 carbon atoms, preferably cyclopentyl or cyclohexyl, especially cyclohexyl. $R_3$ (when n=1) is preferably a monovalent $C_8$–$C_{30}$alkyl radical, and is especially isooctyl, 2-ethylhexyl, n-hexadecyl or n-octadecyl or a mixture of such alkyl radicals. The definitions given here for $R_3$ are also preferred meanings of $R_4$.

When n=2, $R_3$ is preferably $C_2$–$C_8$alkylene, or $C_4$–$C_{12}$alkylene interrupted by oxygen. Accordingly, $R_3$ (when n=2) is an alkylene group derived from a dihydric alcohol by omission of both OH groups, which alkylene group may be interrupted by oxygen. Examples of such dihydric alcohols are alkylene glycols, such as 1,2-ethanediol, 1,3-propanediol, 1,4-butanediol, 1,5-pentanediol, 1,6-hexanediol, 1,7-heptanediol, 1,8-octanediol, polyalkylene glycols, such as diethylene glycol, triethylene glycol and tetraethyleneglycol, dipropylene glycol, tripropylene glycol, or (when n=1) glycerol, pentaerythritol [C(CH$_2$OH)$_4$] or analogous polyols. The n-valent radicals $R_3$ that are interrupted by oxygen can also be derived from etherified polyhydroxy compounds, preferably from polyglycerol or from polypentaerythritol.

In an analogous manner, $R_4$ (when n=2) is preferably an alkylene group derived from a diamine by omission of both H$_2$N groups, which alkylene group may be interrupted by —$NR_5$—, preferably by —NH—. Examples of such diamines include alkylenediamines, such as 1,2-ethylenediamine or 1,2-propylenediamine, and dialkylenediamines, such as di(ethylenediamine) or di(propylenediamine). Di(ethylenediamine), for example, may optionally have a [—NH—($C_mH_{2m}$)—] group on the middle nitrogen atom.

When n=3, $R_3$ is a branched alkylalkylene group derived from a trihydric alcohol by omission of the OH groups. Accordingly $R_3$ is preferably methane-$C_1$–$C_6$alkyltrimethylene. Examples of such trihydric alcohols are 1,1,1-tris-hydroxymethylethane (trimethylolethane) and 1,1,1-tris-hydroxymethylpropane (trimethylolpropane).

When n=4, $R_3$ is a branched alkylalkylene group derived from a tetrahydric alcohol or polyol by omission of the OH groups. Accordingly $R_3$ is preferably methanetetramethylene, for example tetrakis-hydroxymethylmethane (pentaerythritol).

In the alkylene radical —($C_mH_{2m}$)— of the compound of formula (I) and of formula (II), m is preferably two, i.e. the alkylene radical is —CH$_2$CH$_2$—.

There are especially preferably prepared compounds of formula (I) wherein $R_1$ is tert-butyl and $R_2$ is methyl or tert-butyl, and $R_3$ is n-octadecyl, a mixture of higher alkyl radicals having from 8 to 30 carbon atoms ($C_8$–$C_{30}$alkyl radicals) or a radical derived from 1,6-hexanediol, triethylene glycol, pentaerythritol, 1,1,1-tris-hydroxymethylethane or 1,1,1-tris-hydroxymethylpropane, or $R_4$ is a radical derived from 1,2-ethylenediamine or 1,2-propylenediamine or such as di(ethylenediamine) or di(propylenediamine).

The invention relates also to the use of an alkali metal salt of an organic carboxylic acid, or of a mixture of such alkali metal salts, as has been described hereinabove, as a catalyst in the preparation of compounds of formula (I), starting from compounds of formulae (II) and (III), as has been described hereinabove, preference being given to the use of sodium acetate, potassium acetate, lithium acetate, sodium formate, potassium formate or lithium formate or a mixture of such compounds.

The catalyst is added in amounts of from 0.05 to 5 mol %, preferably from 0.05 to 3 mol %, especially from 0.1 to 1 mol %, based on the molar amount of the compound of formula (I) to be reacted.

According to the invention, the process is preferably carried out without solvent, but it is also possible according to the invention for the transesterification to be carried out in an inert organic aliphatic and/or aromatic solvent or in a mixture of such solvents.

According to the invention, the compounds of formula (II) and (III) are heated together with the catalyst under inert conditions, preferably at a temperature of from 90 to 120° C. and with stirring, until a melt is obtained. In order to shift the chemical equilibrium in the transesterification reaction, the pressure is then reduced and the temperature increased, that is to say, the reaction is preferably carried out at a pressure in the range from 0.1 to 200 mbar and at temperatures in the range from 140 to 220° C. The pressure is preferably from 0.1 to 50 mbar, especially from 0.1 to 20 mbar. The reaction temperature is preferably from 160 to 220° C., especially from 165 to 185° C.

The reaction time depends on pressure and the temperature and is generally from 1 to 12 hours, preferably from 1 to 10 hours, especially from 2 to 6 hours.

A small excess of the ester of formula (II) in relation to the hydroxy functions of the alcohol of formula (III) is generally used. The ratio of the compound of formula (II) to the compound of formula (III) [calculated in molar equivalents] is preferably in the range from 0.8:1 to 1.5:1, especially in the range from 1:1 to 1.2:1, and more especially from 1.05:1 to 1.15:1.

When an excess of the compound of formula (II) is used, it is preferably distilled off at the end of the reaction, that excess then also serving as an entraining agent for any undesired secondary components that may be formed that adversely affect the colour of the product (I).

The product of formula (I) can be caused to crystallise or solidify directly by cooling, with or without inoculation, whereupon it can be further processed to its commercial form directly, without an additional purification step, such as recrystallisation. It will be understood that it is also possible according to the invention for the melt to be taken up in a suitable solvent, cooled and, with or without inoculation, crystallised. Suitable solvents include, for example, aliphatic hydrocarbons, such as heptane or cyclohexane or mixtures thereof; aromatic hydrocarbons, such as toluene and/or xylene; alcohols, such as methanol, ethanol, propanol and/or isopropanol, and also the corresponding alcohol/water mixtures (50–100% alcohol). Methanol and/or isopropanol and mixtures thereof with water are preferred.

The residual content of catalyst in the product, for example prior to or subsequent to any filtration of the fully reacted reaction melt that may be carried out, normally does not cause any problems to the use of the product as a stabiliser. Any alkali metal salts present can, however, be removed by means of simple filtration, for example in a manner known per se through a 20 μ filter plate at from 90° C. to 130° C. Following filtration, the content of cataylst is generally in the ppm range.

Particular advantages of the process according to the invention are that the product is obtained in analytically pure form, without any troublesome discoloration, that is to say, without coloured or discoloring secondary components in the reaction melt or in the products, no further purification steps are required and the reaction product can be brought into a usable commercial form by means of physical methods, for example grinding or pelletisation, without the addition of additives.

The compounds of formulae (II) and (III) used in the process according to the invention are known per se. The compounds of formula (I) wherein n=3 and $R_3$ is a trivalent radical derived from 1,1,1-tris-hydroxymethylethane (trimethylolethane), that is to say wherein $R_3$ is 1,1,1-tris-methyleneethane, are novel. Likewise, the compounds of formula (I) wherein n=3 and $R_3$ is a trivalent radical derived from 1,1,1-tris-hydroxymethylpropane (trimethylolpropane), that is to say wherein $R_3$ is 1,1,1-tris-methylenepropane, are novel.

The compounds of formula (I) wherein and $R_3$ is a radical $R_4$—[—$NR_5$—($C_mH_{2m}$)—]$_p$, preferably $R_4$—[NH—($C_mH_{2m}$)—]$_p$, wherein $R_4$ is a radical derived from 1,2-ethylenediamine or 1,2-propylenediamine or from di(ethylenediamine) or di(propylenediamine) and $R_1$, $R_2$ and m are as defined hereinabove, are novel.

The present invention relates also to those compounds. Those compounds can also be prepared by other methods of preparation known per se and are not bound to the preparation process described in the present invention. Surprisingly, the compounds exhibit only a very slight tendency to yellowing in a basic acetone solution, which is an important indicator of the application-related advantages in terms of the Yellowness Index.

The following Examples illustrate the invention further but do not limit the invention:

EXAMPLE 1

β-(3,5-Di-tert-butyl-4-hydroxyphenyl)propionic acid octadecyl ester (Compound of Formula (I) Wherein $R_1$ and $R_2$=tert-butyl, n=1, m=2, $R_3$=n-$C_{18}H_{37}$)

109 g (0.374 mol) of β-(3,5-di-tert-butyl4-hydroxyphenyl)propionic acid methyl ester, 92.5 g (0.34 mol) of stearyl alcohol and 0.1 g of lithium acetate in the dihydrate form (0.001 mol) are introduced into a vessel and melted and stirred at 100° C. under nitrogen. As soon as a melt is obtained, cautiously evacuation is carried out and at the same time the melt is heated to an internal temperature (IT) of from 150 to 160° C. The methanol formed is distilled off and condensed in a cold trap. As soon as an internal pressure of <10 mbar is reached, the internal temperature (IT) is increased to from 170 to 180° C. and further evacuation to <1 mbar is carried out. As soon as IT=180° C. and a pressure of <1 mbar is reached, those conditions are maintained for one hour and then, in the course of from 1 to 2 hours at IT=200–210° C., the excess β-(3,5-di-tert-butyl-4-hydroxyphenyl)propionic acid methyl ester is removed by distillation. The reaction melt then contains <0.2% starting materials and has a content of >98% β-(3,5-di-tert-butyl-4-hydroxyphenyl)propionic acid octadecyl ester. The reaction melt is cooled, and left to stand for crystallisation. Yield 96.5%; m.p. 51° C.

EXAMPLE 2

β-(3,5-Di-tert-butyl-4-hydroxyphenyl)propionic acid octadecyl ester (Compound of Formula (I) wherein $R_1$ and $R_2$=tert-butyl, n=1, m=2, $R_3$=n-$C_{18}H_{37}$)

109 g (0.374 mol) of β-(3,5-di-tert-butyl-4-hydroxyphenyl)propionic acid methyl ester, 92.5 g (0.34 mol) of stearyl alcohol and 0.2 g of sodium formate (0.003 mol) are introduced into a vessel and melted and stirred at 100° C. under nitrogen. As soon as a melt is obtained, cautiously evacuation is carried out and at the same time the melt is heated to an internal temperature of from 150 to 160° C. The methanol formed is distilled off and condensed in a cold trap. As soon as an internal pressure of <10 mbar is reached, the internal temperature is increased to from 170 to 180° C. and further evacuation to <1 mbar is carried out. As soon as IT=180° and a pressure of <1 mbar is reached, those conditions are maintained for one hour and then, in the course of from 1 to 2 hours at IT=200–210° C., the excess β-(3,5-di-tert-butyl-4-hydroxyphenyl)propionic acid methyl ester is removed by distillation. The reaction melt then contains <0.2% starting materials and has a content of >98% β-(3,5-di-tert-butyl-4-hydroxyphenyl)propionic acid octadecyl ester. The reaction melt is cooled, and left to stand for crystallisation. Yield 96.5%; m.p. 51° C.

EXAMPLE 3

Triethyleneglycyl bis[β-(3,5-di-tert-butyl-4-hydroxyphenyl)propionic acid] ester (Compound of Formula (I) wherein $R_1$ and $R_2$=tert-butyl, n=2, m=2, $R_3$=—($CH_2CH_2O)_2CH_2CH_2$—)

76 g (0.26 mol) of β-(3,5-di-tert-butyl-4-hydroxyphenyl) propionic acid methyl ester, 15 g (0.1 mol) of triethylene glycol and 0.17 g of lithium acetate in the dihydrate form (0.0015 mol) are introduced into a vessel and melted and stirred at 100° C. under nitrogen. As soon as a melt is obtained, cautiously evacuation is carried out and at the same time the melt is heated to an internal temperature of from 160 to 180° C. The methanol formed is distilled off and condensed in a cold trap. As soon as an internal pressure of <10 mbar is reached, the internal temperature is increased to from 180 to 190° C. and further evacuation to <1 mbar is carried out. As soon as IT=190° and a pressure of <1 mbar is reached, those conditions are maintained for one hour and then, in the course of from 1 to 2 hours at IT=200–220° C., the excess β-(3,5-di-tert-butyl-4-hydroxyphenyl)propionic acid methyl ester is removed by distillation. The reaction melt then contains <0.2% starting materials and has a content of >97% triethyleneglycyl bis[β-(3,5-di-tert-butyl- 4-hydroxyphenyl)propionic acid] ester. The reaction melt is cooled, and left to stand for crystallisation. Yield 94%; m.p. 113–115° C.

EXAMPLE 4

Triethyleneglycyl bis[β-(3-tert-butyl-5-methyl-4-hydroxyphenyl)propionic acid] ester (Compound of Formula (I) wherein $R_1$=tert-butyl, $R_2$=methyl, n=2, m=2, $R_3$=—($CH_2CH_2O)_2CH_2CH_2$)—)

65 g (0.26 mol) of β-(3-tert-butyl-5-methyl-4-hydroxyphenyl)propionic acid methyl ester, 15 g (0.1 mol) of triethylene glycol and 0.17 g of lithium acetate in the dihydrate form (0.0015 mol) are introduced into a vessel and melted and stirred at 100° C. under nitrogen. As soon as a melt is obtained, cautiously evacuation is carried out and at the same time the melt is heated to an internal temperature of from 160 to 170° C. The methanol formed is distilled off and condensed in a cold trap. As soon as an internal pressure of <10 mbar is reached, the internal temperature is increased to from 170 to 180° C. and further evacuation to <1 mbar is carried out. As soon as IT=180° and a pressure of <1 mbar is reached, those conditions are maintained for one hour and then, in the course of from 1 to 2 hours at IT=190–200° C., the excess β-(3-tert-butyl-5-methyl-4-hydroxyphenyl)propionic acid methyl ester is removed by distillation. The reaction melt then contains <0.2% starting materials and has a content of >97% triethyleneglycyl bis[β-(3-tert-butyl-5-methyl-4-hydroxyphenyl)propionic acid] ester. The reaction melt is cooled, and left to stand for crystallisation. Yield 94.5%; m.p. 74–77° C.

EXAMPLE 5

1,1,1-Tris[β-(3,5-di-tert-butyl-4-hydroxyphenyl) propionyloxymethyl]propane (Compound of Formula (I) wherein $R_1$ and $R_2$=tert-butyl, n=3, m=2, $R_3$=$CH_3CH_2C(CH_2)_3$)

85.5 g (0.293 mol) of β-(3,5-di-tert-butyl-4-hydroxyphenyl)propionic acid methyl ester, 10.1 g (0.075 mol) of 1,1,1-tris(hydroxymethyl)propane and 0.23 g of lithium acetate in the dihydrate form (0.002 mol) are introduced into a vessel and melted and stirred at 120° C. under nitrogen. As soon as a melt is obtained, cautiously evacuation is carried out and at the same time the melt is heated to an internal temperature of 160° C. The methanol formed is distilled off and condensed in a cold trap. As soon as an internal pressure of <10 mbar is reached, the internal temperature is increased to 180° C. and further evacuation to <1 mbar is carried out. As soon as IT=180° and a pressure of <1 mbar is reached, those conditions are maintained for one hour and then, in the course of from 1 to 2 hours at IT=200–210° C., the excess β-(3,5-di-tert-butyl-4-hydroxyphenyl)-propionic acid methyl ester is removed by distillation. The reaction melt then contains <0.2% β-(3,5-di-tert-butyl-4-hydroxyphenyl)-propionic acid methyl ester and has a content of >97% 1,1,1-tris[β-(3,5-di-tert-butyl4-hydroxyphenyl)propionyloxymethyl]propane. The colourless reaction melt is filtered, cooled and caused to solidify/crystallise. Yield 95%; m.p. 66–79° C. (amorphous form).

EXAMPLE 6

1,1,1-Tris[β-(3,5-di-tert-butyl4-hydroxyphenyl) propionyloxymethyl]propane (Compound of Formula (I) wherein $R_1$ and $R_2$=tert-butyl, n=3, m=2, $R_3$=$CH_3CH_2C(CH_2)_3$)

85.5 g (0.293 mol) of β-(3,5-di-tert-butyl-4-hydroxyphenyl)propionic acid methyl ester, 10.1 g (0.075 mol) of 1,1,1-tris(hydroxymethyl)propane and 0.19 g of sodium acetate (0.002 mol) are introduced into a vessel and melted and stirred at 120° C. under nitrogen. As soon as a melt is obtained, cautiously evacuation is carried out and at the same time the melt is heated to an internal temperature of 160° C. The methanol formed is distilled off and condensed in a cold trap. As soon as an internal pressure of <10 mbar is reached, the internal temperature is increased to 180° C. and further evacuation to <1 mbar is carried out. As soon as IT=180° and a pressure of <1 mbar is reached, those conditions are maintained for one hour and then, in the course of from 1 to 2 hours at IT=200–210° C., the excess β-(3,5-di-tert-butyl-4-hydroxyphenyl)propionic acid methyl ester is removed by distillation. The reaction melt then contains <0.2% β-(3,5-di-tert-butyl-4-hydroxyphenyl) propionic acid methyl ester and has a content of >97% 1,1,1-tris[β-(3,5-di-tert-butyl-4-hydroxyphenyl) propionyloxymethyl]propane. The colourless reaction melt is filtered, cooled and caused to solidify/crystallise. Yield 95.5%; m.p. 66–79° C. (amorphous form).

EXAMPLE 7

1,1,1-Tris[β-(3,5-di-tert-butyl-4-hydroxyphenyl) propionyloxymethy]ethane (Compound of Formula (I) wherein $R_1$ and $R_2$=tert-butyl, n=3, m=2, $R_3$= $CH_3C(CH_2)_3$)

85.5 g (0.293 mol) of β-(3,5-di-tert-butyl-4-hydroxyphenyl)propionic acid methyl ester, 9 g (0.075 mol) of 1,1,1-tris(hydroxymethyl)ethane and 0.23 g of lithium acetate in the dihydrate form (0.002 mol) are introduced into a vessel and melted and stirred at 120° C. under nitrogen. As soon as a melt is obtained, cautiously evacuation is carried out and at the same time the melt is heated to an internal temperature of 160° C. The methanol formed is distilled off and condensed in a cold trap. As soon as an internal pressure of <10 mbar is reached, the internal temperature is increased to 180° C. and further evacuation to <1 mbar is carried out. As soon as IT=180° and a pressure of <1 mbar is reached, those conditions are maintained for one hour and then, in the course of from 1 to 2 hours at IT=200–210° C., the excess β-(3,5-di-tert-butyl-4-hydroxyphenyl)propionic acid methyl ester is removed by distillation. The reaction melt then contains <0.2% β-(3,5-di-tert-butyl-4-hydroxyphenyl)-propionic acid methyl ester and has a content of >97% 1,1,1-tris[β-(3,5-di-tert-butyl-4-hydroxyphenyl) propionyloxymethyl]ethane. The colourless reaction melt is filtered, cooled and caused to solidify/crystallise. Yield 95%; m.p. 55–78° C. (amorphous form).

EXAMPLE 8

Tetrakis[β-(3,5-di-tert-butyl-4-hydroxyphenyl) propionyloxymethyl]methane (Compound of Formula (I) wherein $R_1$ and $R_2$=tert-butyl, n=4, m=2, $R_3$=$C(CH_2)_4$)

75.9 g (0.26 mol) of β-(3,5-di-tert-butyl-4-hydroxyphenyl)propionic acid methyl ester, 6.8 g (0.05 mol) of pentaerythritol and 0.16 g of sodium acetate (0.002 mol) are introduced into a vessel and melted and stirred at 120° C. under nitrogen. As soon as a melt is obtained, cautiously evacuation is carried out and at the same time the melt is heated to an internal temperature of from 160 to 170° C. The methanol formed is distilled off and condensed in a cold trap. As soon as an internal pressure of <10 mbar is reached, the internal temperature is increased to 180° C. and further evacuation to <1 mbar is carried out. As soon as IT=180° C.

and a pressure of <1 mbar is reached, those conditions are maintained for one hour and then, in the course of from 1 to 2 hours at IT=200–210° C., the excess β-(3,5-di-tert-butyl-4-hydroxyphenyl)propionic acid methyl ester is removed by distillation. The reaction melt then contains <0.2% β-(3,5-di-tert-butyl-4-hydroxyphenyl)propionic acid methyl ester and has a content of >96% tetrakis[β-(3,5-di-tert-butyl-4-hydroxyphenyl)propionyloxymethyl]methane. The colourless reaction melt is filtered, cooled and caused to solidify/crystallise. Yield 96%; m.p. 55–85° C. (amorphous form).

What is claimed is:

1. A process for the preparation of a compound of formula (I)

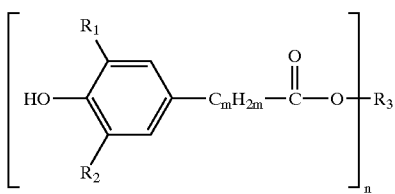

wherein
$R_1$ and $R_2$ are each independently of the other $C_1$–$C_8$alkyl, cyclopentyl or cyclohexyl,
m is 1, 2 or 3,
n is an integer from 1 to 30, and
$R_3$ is an n-valent radical from linear or branched $C_4$–$C_{30}$alkyl, which is optionally interrupted by oxygen, or (when n=1–12) an n-valent radical from $C_5$–$C_{12}$cycloalkyl, or a radical $R_4$—[$NR_5$—($C_mH_{2m}$)—]$_p$,
$R_4$ is hydrogen, an n-valent radical from linear or branched $C_4$–$C_{30}$alkyl, which is optionally interrupted by the group —$NR_5$—, or (when n=1–12) an n-valent radical from $C_5$–$C_{12}$cycloalkyl,
$R_5$ radicals, each independently of any other(s), are hydrogen or methyl or —($C_mH_{2m}$)—, and
p corresponds to the number of —[$NR_5$—($C_mH_{2m}$)—] groups that gives n —($C_mH_{2m}$)— radicals per molecule, by reaction of a compound of formula (II)

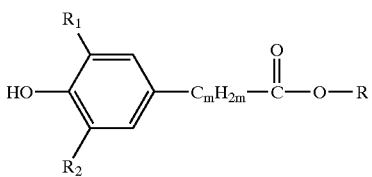

wherein R is $C_1$–$C_3$alkyl,
with a compound of formula (III)

$R_3(OH)_n$ (III)

wherein $R_3$ and n are as defined above,
wherein the reaction takes place at a practically neutral acid value (pH) and in the presence of a catalyst,
wherein the catalyst is an alkali metal salt of an organic carboxylic acid or is a mixture of said salts, which salt or salts are dissolved or suspended in the reaction mixture, wherein (i) the alkali metal salt is formed from an alkali metal cation and an anion of an organic carboxylic acid and (ii) the organic carboxylic acid is at least partially volatile under the reaction conditions applied.

2. A process according to claim 1, wherein the catalyst is a sodium, potassium or lithium salt, or are a mixture of said salts.

3. A process according to claim 1, wherein the carboxylic acid from which the alkali metal salt is formed is an aliphatic, saturated or unsaturated carboxylic acid having from 2 to 10 carbon atoms.

4. A process according to claim 3, wherein the carboxylic acid is selected from the group formic acid, acetic acid, propionic acid, n-butyric acid, isobutyric acid, n-valeric acid, trimethylacetic acid, caproic acid, n-heptanoic acid, pelargonic acid, malonic acid, maleic acid, fumaric acid, malonic acid monomethyl ester, fluoroacetic acid, chloroacetic acid, bromoacetic acid, difluoroacetic acid, dichloroacetic acid, trifluoroacetic acid, trichloroacetic acid, α-chloropropionic acid and β-chloropropionic acid.

5. A process according to claim 1, wherein sodium acetate, potassium acetate, lithium acetate, sodium formate, potassium formate or lithium formate or a mixture of said compounds are present as catalyst.

6. A process according to claim 1, wherein $R_1$ is linear or branched $C_1$–$C_4$alkyl.

7. A process according to claim 1, wherein $R_2$ is linear or branched $C_1$–$C_4$alkyl.

8. A process according to claim 6, wherein in the compound of formula (I) $R_1$ and $R_2$ are different.

9. A process according to claim 1, wherein $R_4$—[$NR_5$—($C_mH_{2m}$)—]$_p$ is a radical $R_4$—[NH—($C_mH_{2m}$)—]$_p$ or $R_4$—[N($C_mH_{2m}$)$_2$—]$_p$, and $R_4$ is derived from an alkylenediamine, or from a polyalkylenediamine.

10. A process according to claim 1, wherein $R_3$ is n-butyl, isobutyl, tert-butyl, pentyl, isopentyl, hexyl, heptyl, octyl, 2-ethylhexyl, nonyl, decyl, undecyl, dodecyl, tridecyl, tetradecyl, pentadecyl, hexadecyl, heptadecyl, octadecyl, eicosyl or a corresponding homologous radical having carbon atoms increasing to 30 carbon atoms or a mixture of $C_4$–$C_{30}$ radicals, or cyclopentyl or cyclohexyl.

11. A process according to claim 1, wherein $R_3$ is a radical derived from a dihydric alcohol by omission of the OH groups, where the alcohol is 1,2-ethanediol, 1,3-propanediol, 1,4-butanediol, 1,5-pentanediol, 1,6-hexanediol, 1,7-heptanediol or 1,8-octanediol, diethylene glycol, triethylene glycol or tetraethylene glycol, dipropylene glycol or tripropylene glycol, glycerol, pentaerythritol or an analogous polyol or polyglycerol or polypentaerythritol.

12. A process according to claim 1, wherein $R_4$ is an alkylene group derived from a diamine by omission of both $H_2N$ groups, which alkylene group is optionally interrupted by —$NR_5$—, where the diamine is 1,2-ethylenediamine, 1,2-propylenediamine, di(ethylenediamine) or di(propylenediamine).

13. A process according to claim 1, wherein $R_3$ is a branched alkylalkylene radical derived from a trihydric alcohol (polyol) by omission of the OH groups, where the alcohol is 1,1,1-tris-hydroxymethylethane (trimethylolethane) or 1,1,1-tris-hydroxymethylpropane (trimethylolpropane).

14. A process according to claim 1, wherein $R_3$ is methanetetramethylene.

15. A process according to claim 1, wherein, in the compound of formula (I), $R_1$ is tert-butyl and $R_2$ is methyl or tert-butyl, and $R_3$ is n-octadecyl, a mixture of higher alkyl radicals having from 8 to 30 carbon atoms or a radical derived from 1,6-hexanediol, triethylene glycol, pentaerythritol, 1,1,1-tris-hydroxymethylethane or 1,1,1-tris-hydroxymethylpropane.

16. A process according to claim 1, wherein, in the compound of formula (I), $R_1$ is tert-butyl and $R_2$ is methyl or tert-butyl, and $R_4$ is a radical derived from 1,2-ethylenediamine or 1,2-propylenediamine or from di(ethylenediamine) or di(propylenediamine).

17. A process according to claim 1, wherein the compounds of formulae (II) and (III) are heated together with the catalyst at a temperature of from 90 to 120° C., until a melt is obtained and the transesterification reaction is then carried out at reduced pressure in the range from 0.1 to 200 mbar and at elevated temperature in the range from 140 to 220° C.

18. A process according to claim 1, wherein the ratio of the compound of formula (II) to the compound of formula (III) [calculated in molar equivalents] is in the range from 0.8:1 to 1.5:1.

19. A process according to claim 1, wherein the product of formula (I) is caused to crystallise or solidify by cooling, with or without inoculation, and is further processed to its commercial form directly, without an additional purification step.

20. A compound of formula (I)

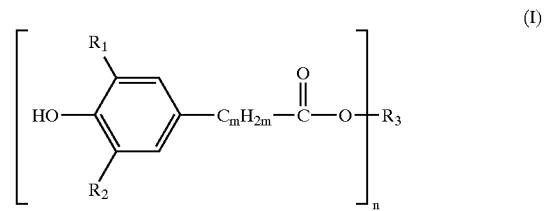

wherein $R_1$ and $R_2$ are each independently of the other $C_1$–$C_8$alkyl, cyclopentyl or cyclohexyl, m is 1, 2 or 3, $R_3$ is a radical $R_4$—[$NR_5$—($C_mH_{2m}$)—]$_p$, wherein $R_4$ is a radical derived from 1,2-ethylenediamine or 1,2-propylenediamine or from di(ethylenediamine) or di(propylenediamine), $R_5$ is independently hydrogen or methyl, and p and n are as defined in claim 1.

* * * * *